(12) United States Patent
Yuge et al.

(10) Patent No.: US 11,219,544 B2
(45) Date of Patent: Jan. 11, 2022

(54) WALKING MOTION ASSIST DEVICE (71) Applicant: Space Bio-Laboratories Co., Ltd., Hiroshima (JP)

(72) Inventors: Rui Yuge, Hiroshima (JP); Yumi Kawahara, Hiroshima (JP)

(73) Assignee: Space Bio-Laboratories Co., Ltd., Hiroshima (JP)

( * ) Notice: Subject to any disclaimer, the term of this patent is extended or adjusted under 35 U.S.C. 154(b) by 289 days.

(21) Appl. No.: 16/303,563

(22) PCT Filed: Nov. 28, 2016

(86) PCT No.: PCT/JP2016/085113
§ 371 (c)(1),
(2) Date: Nov. 20, 2018

(87) PCT Pub. No.: WO2017/208480
PCT Pub. Date: Dec. 7, 2017

(65) Prior Publication Data
US 2019/0314185 A1 Oct. 17, 2019

(30) Foreign Application Priority Data
Jun. 2, 2016 (JP) .............................. JP2016-111378

(51) Int. Cl.
*A61F 5/01* (2006.01)
*A61H 3/00* (2006.01)
(Continued)

(52) U.S. Cl.
CPC .............. *A61F 5/0111* (2013.01); *A61H 3/00* (2013.01); *A63B 23/08* (2013.01); *A61B 5/112* (2013.01); *A61H 2003/007* (2013.01)

(58) Field of Classification Search
CPC .... A61H 2201/5071; A61H 2201/1671; A61H 2201/165; A61H 2201/5069;
(Continued)

(56) References Cited

U.S. PATENT DOCUMENTS

2011/0205067 A1\* 8/2011 Konishi ................. A61H 1/024
340/573.1
2015/0157525 A1 6/2015 Choi et al.
(Continued)

FOREIGN PATENT DOCUMENTS

JP 2010148759 A 7/2010
JP 2011206289 A 10/2011
(Continued)

OTHER PUBLICATIONS

International Search Report and Written Opinion (International Application No. PCT/JP2016/085113); dated Jan. 10, 2017; 9 pages.
International Robot Exhibition 2015 (iREX 2015); http:biz.nikkan.co.jp/eve/irex/; A brochure distributed on Dec. 2, 2015; 5 pages.
Office Action (CA Application No. 3,026,020); dated Nov. 19, 2019; 5 pages.
(Continued)

*Primary Examiner* — Timothy A Stanis
*Assistant Examiner* — Matthew R Moon
(74) *Attorney, Agent, or Firm* — Howard & Howard Attorneys PLLC (57) ABSTRACT

A device for assisting a wearer in rotationally moving an ankle joint. A drive mechanism coaxially rotates with the ankle joint using a drive motor; a control device controls the drive motor. A storage stores a basic movement pattern and a corrected movement pattern that represent time-series changes in ankle joint angle in a gait cycled. A calculator obtains the corrected movement pattern by correcting the basic movement pattern based on input operation. The basic movement pattern is represented by a polygonal line or a Bézier curve, each of which includes a plurality of predetermined points serving as inflection points, or a combina-
(Continued)

tion of thereof. The calculator generates the corrected movement pattern corrected by adjusting positions of the plurality of predetermined points on the basic movement pattern, and, based on the corrected movement pattern, the control device controls driving provided by the drive motor.

5 Claims, 7 Drawing Sheets

(51) Int. Cl.
*A63B 23/08* (2006.01)
*A61B 5/11* (2006.01)

(58) Field of Classification Search
CPC ........ A61H 2205/12; A61H 2201/1215; A61H 2205/106; A61H 2201/5007; A61B 5/1071
See application file for complete search history.

(56) References Cited

U.S. PATENT DOCUMENTS

| | | | |
|---|---|---|---|
| 2016/0058646 A1* | 3/2016 | Seo | A61H 3/00 623/32 |
| 2017/0273853 A1* | 9/2017 | Nagata | A61B 5/1038 |
| 2018/0160946 A1* | 6/2018 | Macko | A61B 5/112 |

FOREIGN PATENT DOCUMENTS

| | | | | |
|---|---|---|---|---|
| JP | 2012213554 A | | 11/2012 | |
| JP | 5189911 B2 | | 4/2013 | |
| JP | 2014226151 A | | 12/2014 | |
| JP | 2015058033 A | * | 3/2015 | |
| JP | 2015058033 A | | 3/2015 | |

OTHER PUBLICATIONS

Extended European Search Report (EP Application No. 16904104.3-1126) dated Dec. 2, 2019; 8 pages.

* cited by examiner

WALKING MOTION ASSIST DEVICE

CROSS-REFERENCE TO RELATED APPLICATIONS

This application is a national phase application of International Patent Application No. PCT/JP2016/085113, filed Nov. 28, 2016, which claims priority to JP Patent Application No. 2016-111378, filed Jun. 2, 2016, the disclosures of which are hereby incorporated by reference in their entirety.

TECHNICAL FIELD

The present disclosure relates to a walking motion assist device.

BACKGROUND ART

Walking motion assist devices are made available for rehabilitation of paralytics and other disabled persons, intended to correct walking motions of such persons so that the corrected motions approximate to those of healthy people. Such a walking motion assist device is attached to a lower limb of the wearer such as a paralytic patient to correct joint movement of the wearer so that the corrected movement approximates to that of a healthy person.

The walking motion assist device described in Patent Literature 1 controls the movement pattern that has been obtained by detecting motion state quantities (ankle joint angles) in time series during a gait cycle of the wearer so that the obtained movement pattern approximates to the movement pattern (the reference movement pattern) of a healthy person.

CITATION LIST

Patent Literature

Patent Literature 1: Unexamined Japanese Patent Application Kokai Publication No. 2015-58033.

SUMMARY OF INVENTION

Technical Problem

The device described in Patent Literature 1 necessitates changing the target ankle joint angle value for every one of multiple (16, for example) detection periods adjacent to each other in time series, in order to obtain data on continuous ankle joint angular changes. Thus, the device poses a problem associated with a long correction time on site, causing difficulty in smooth gait training.

The present disclosure has been made in view of the foregoing circumstances, and an objective of the disclosure is to provide a walking motion assist device that allows for smooth gait training.

Solution to Problem

A walking motion assist device according to the present disclosure assists a wearer in rotationally moving an ankle joint of the wearer. The walking motion assist device includes: a drive motor; a drive mechanism that is capable of rotating coaxially with the ankle joint by way of the drive motor; a control device that controls driving provided by the drive motor; a storage that stores a basic movement pattern and a corrected movement pattern that represent time-series changes in ankle joint angle in a gait cycle; and a calculator that obtains the corrected movement pattern by correcting the basic movement pattern based on input by an operator, wherein the basic movement pattern is represented by a polygonal line or a Bezier curve, each of which includes a plurality of predetermined points serving as inflection points, or a combination of the polygonal line and the Bezier curve, wherein the calculator generates the corrected movement pattern corrected by adjusting positions of the plurality of predetermined points on the basic movement pattern, and wherein the control device controls driving provided by the drive motor based on the corrected movement pattern.

The plurality of predetermined points are preferably four points corresponding to heel and toe contact, heel off, toe off, and midswing, respectively, in a gait cycle.

The basic movement pattern and the corrected movement pattern each may be represented by a polygonal line that includes the four points serving as inflection points.

The control device preferably controls an angular velocity of the ankle joint in conformance with the basic movement pattern or the corrected movement pattern.

Preferably, the walking motion assist device includes:
a heel-side pressure sensor that detects heelstrike and heel off of the wearer; and a toe-side pressure sensor that detects toe contact and toe off of the wearer,
wherein the heel-side pressure sensor and the toe-side pressure sensor detect a load of the heel and a load of the toe, respectively, when the wearer is in a standing position, and
wherein, based on the load detected when the wearer is in the standing position, a state of the heelstrike, the toe contact, the heel off, and the toe off of the wearer in walking motion is detected.

Preferably, as a starting point of a gait cycle, from a point of time when the heel-side pressure sensor detects the heelstrike of the wearer, the control device controls driving provided by the drive motor based on the basic movement pattern or the corrected movement pattern.

Preferably, the walking motion assist device includes a rotation sensor that detects an ankle joint angle of the wearer,
wherein, assuming that a starting point and an end point of a single step gait cycle correspond to the heelstrike and the next heelstrike, respectively, the control device uses the ankle joint angle detected by the rotation sensor at the end point of an n-th step as the ankle joint angle at the starting point of an (n+1)th step to adjust the basic movement pattern or the corrected movement pattern for the (n+1)th step and controls the drive motor (where n represents a positive integer).

Advantageous Effects of Invention

The walking motion assist device according to the present disclosure achieves a shorter correction time on a rehabilitation site and smoother gait training.

DESCRIPTION OF EMBODIMENTS

Figure 1:
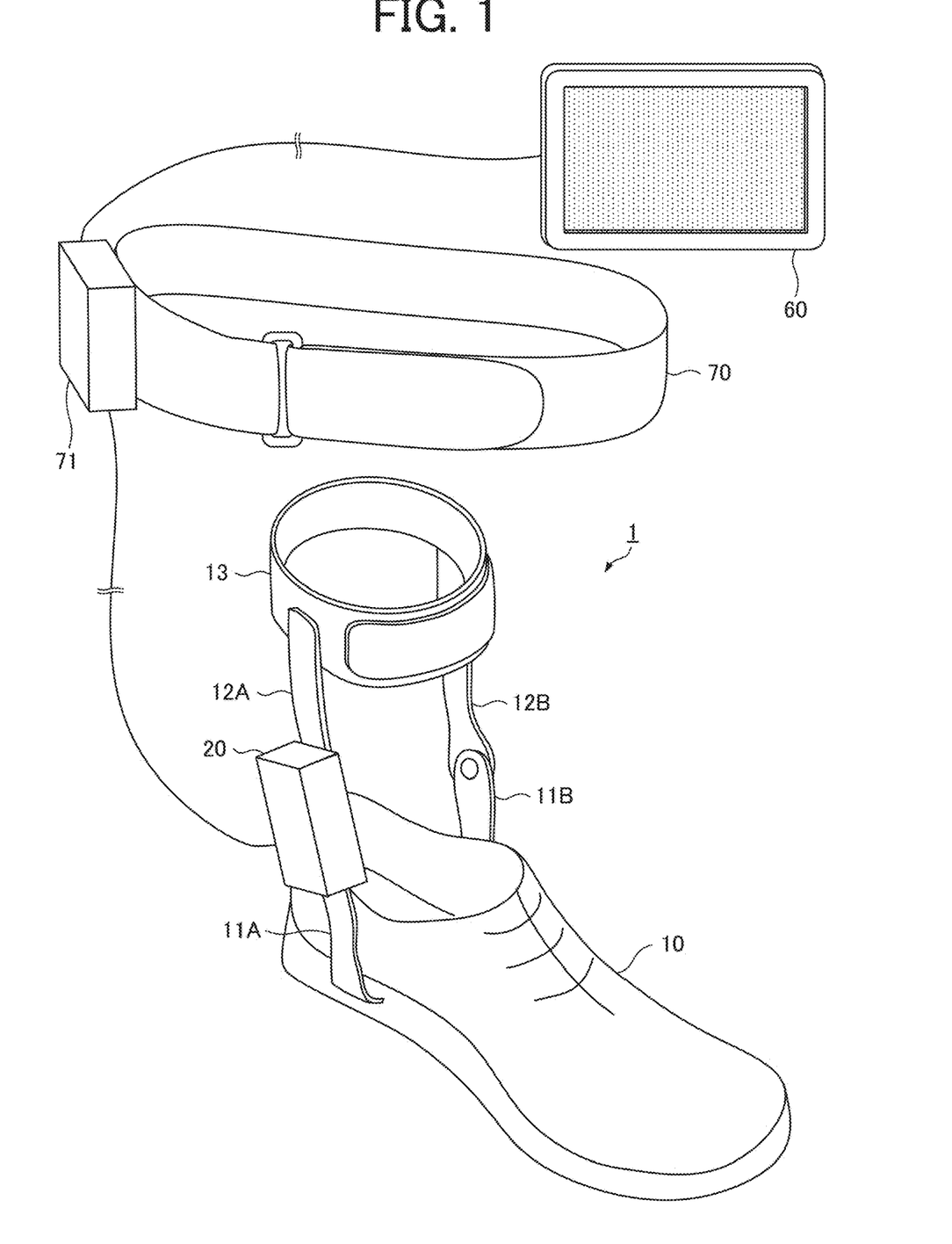
FIG. 1 is a perspective view of a walking motion assist device.
Figure 2:
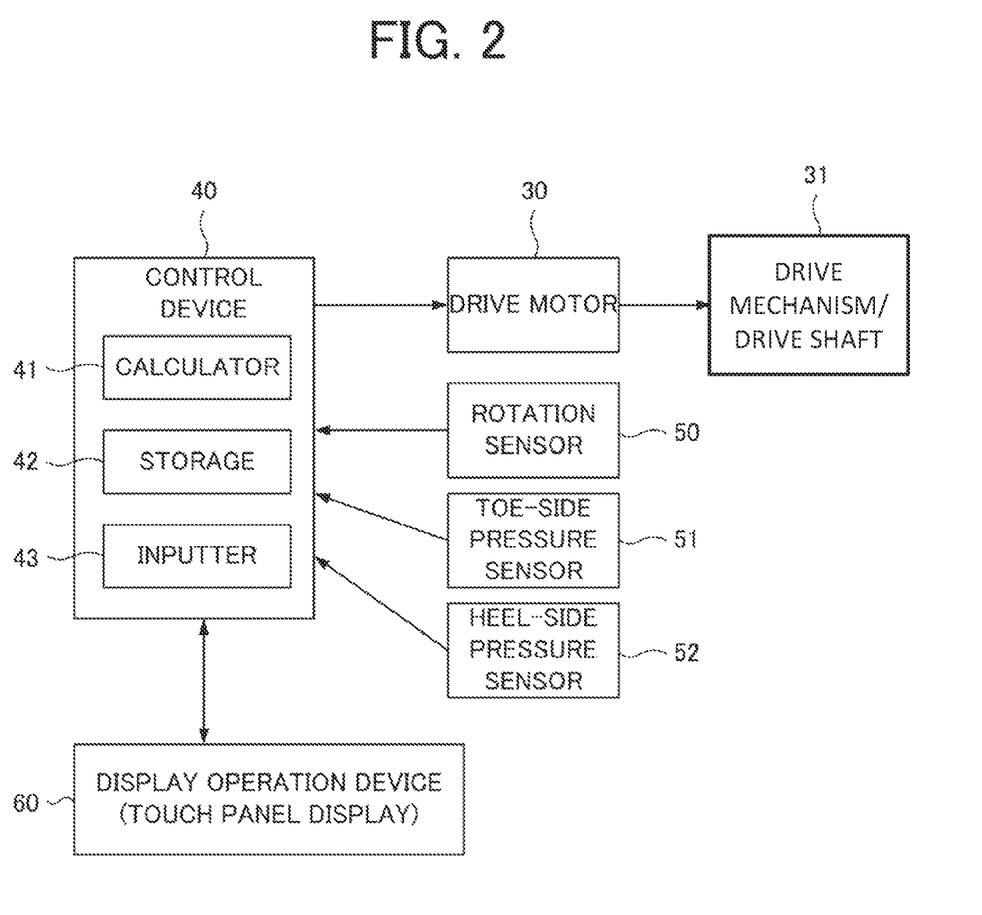
FIG. 2 is a block diagram conceptually illustrating a control system in the walking motion assist device.
Figure 3:
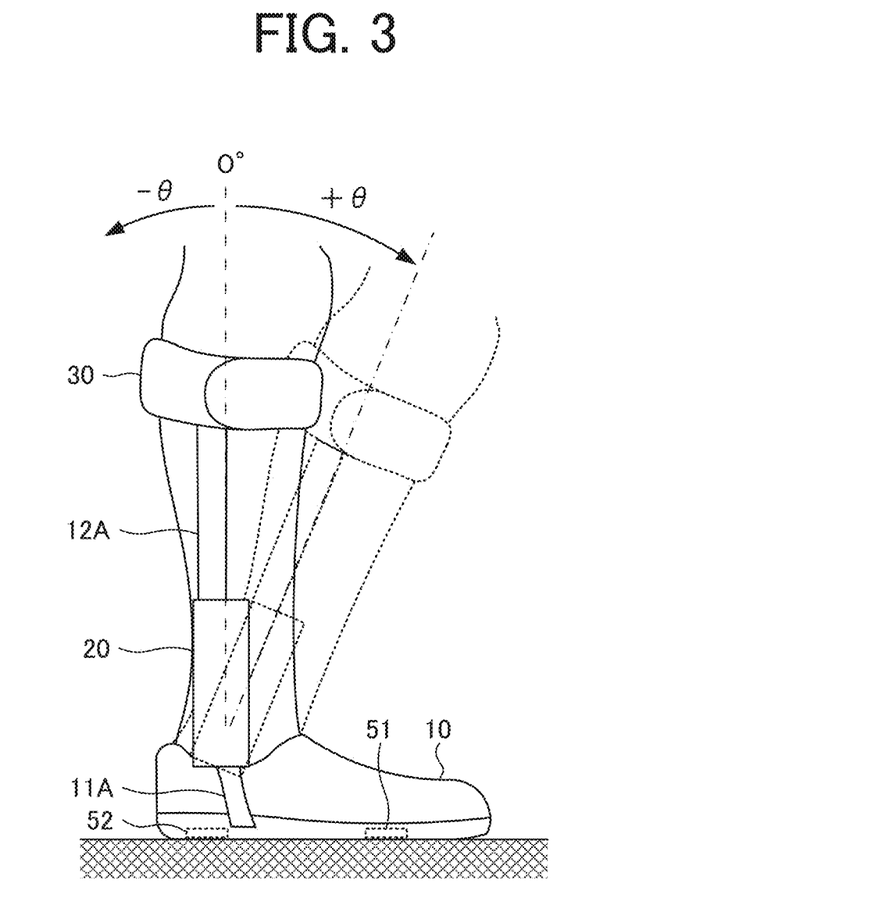
FIG. 3 illustrates varying ankle joint angles when the walking motion assist device is worn.

A walking motion assist device according to the present embodiment will now be described with reference to the drawings. As illustrated in FIGS. 1 to 3, the walking motion assist device 1 includes a foot brace 10, foot frames 11A, 11B, shank frames 12A, 12B, a shank brace 13, a shank container box 20, a drive motor 30, a drive mechanism 31, a rotation sensor 50, a toe-side pressure sensor 51, a heel-side pressure sensor 52, a display operation device 60, a waist brace 70, and a waist container box 71.

The foot brace 10, which is in the form of a shoe to be worn on the wearer's foot, is attached to the foot that is inserted therein such that the foot is in a fixed posture.

The foot frames 11A, 11B are disposed on the foot brace 10. The foot frames 11A, 11B are fastened so as not to move relative to the foot brace 10.

On the bottom of the foot brace 10, the toe-side pressure sensor 51 and the heel-side pressure sensor 52 are disposed. The toe-side pressure sensor 51 is disposed on the bottom near the thenar portion of the foot brace 10. The toe-side pressure sensor 52 detects a load applied by the wearer's toes. The heel-side pressure sensor 52 is disposed on the bottom near the heel portion of the foot brace 10. The heel-side pressure sensor 52 detects a load applied by the wearer's heel. The toe-side pressure sensor 51 and the heel-side pressure sensor 52 are communicatively connected to a control device 40 in a wired or wireless manner.

The shank brace 13, which is worn on the wearer's shank with the shank brace 13 wound around the shank, is stably attached to a portion lower than the wearer's knee.

Upper portions of the shank frames 12A, 12B are disposed on the shank brace 13. The shank frames 12A, 12B are fastened so as not to move relative to the shank brace 13.

Upper portions of the foot frames 11A, 11B and lower portions of the shank frames 12A, 12B are connected via pivots or the like placed coaxially with the rotational axis of the ankle joint of the wearer. Thus, the shank frames 12A, 12B are connected with the foot frames 11A, 11B so as to be rotatable coaxially with the ankle joint of wearer.

The shank container box 20 is disposed on the shank frame 11A. The shank container box 20 contains the drive motor 30, the drive mechanism 31, and the rotation sensor 50.

The drive motor 30 mechanically transmits a rotational driving force to the drive mechanism 31. Using the rotational driving force transmitted by the drive motor 30, the drive mechanism 31 causes the foot frame 11A to move rotationally relative to the shank frame 12A. In this way, the drive motor 30 and the drive mechanism 31 assist the wearer in rotationally moving the ankle joint of wearer.

The rotation sensor 50 is disposed coaxially with, for example, the drive shaft of the drive mechanism 31. The rotation sensor 50 detects a rotation angle of the ankle joint of wearer by obtaining a crossing angle between an axis extending from the foot frame 11A and an axis extending from the shank frame 12B. As illustrated in FIG. 3, using the ankle joint angle at midstance as the reference angle (0°), the rotation sensor 50 detects an angle +θ when the ankle joint is plantarflexed from the reference angle and an angle −θ when the ankle joint is dorsiflexed from the reference angle. The rotation sensor 50 is communicatively connected to the control device 40 in a wired or wireless manner.

The display operation device 60, which may be a touch-panel device, for example, is used for operations carried out by an operator such as a physical therapist. The display operation device 60 shows a polygonal line or a Bézier curve, each of which includes a plurality of predetermined points serving as inflection points, or a combination thereof, as a basic movement pattern or a corrected movement pattern. Basic movement patterns and corrected movement patterns each are a pattern showing time-series relationships between ankle joint angles (θ) and gait phases in a single gait cycle. The plurality of points are the points at which the rotational direction of the ankle joint is changed. The operator can move the plurality of points on a basic movement pattern. The display operation device 60 is communicatively connected to the control device 40 in a wired or wireless manner.

With reference to FIG. 1 again, the waist container box 71 is disposed on the waist brace 70. The waist brace 70, which is worn on the wearer's waist with the waist brace 70 wound around the waist, is stably attached at the position of the wearer's waist to hold the waist container box 71.

The waist container box 71 contains the control device 40 and a battery (not illustrated).

The control device 40 includes a calculator 41, a storage 42, and an inputter 43. As described later, based on the parameters: angle, angular velocity, and torque, the control device 40 controls the rotation and the rotating torque produced by the drive motor 30, thereby controlling the ankle joint of the wearer of the walking motion assist device 1 when the wearer is in walking motion.

The calculator 41, which is a central processor unit (CPU), fulfils functions of the whole walking motion assist device 1 by executing a program stored in the storage 42. In addition, the calculator 41 has the function to correct a basic movement pattern to obtain a corrected movement pattern as described below, as well as the function to control the whole walking motion assist device 1.

The storage 42 is a non-volatile storage device such as read-only memory (ROM), random-access memory (RAM), or flash memory. The storage 42 contains a program for controlling operations of the calculator 41. The storage 42 stores a plurality of (four, for example) basic movement patterns each representing time-series changes in ankle joint angle in a single gait cycle. As described later, the storage 42 further stores a corrected movement pattern obtained by correcting any of the basic movement patterns.

Information from the display operation device 60 is input to the inputter 43, and results of detection by the rotation sensor 50, the toe-side pressure sensor 51, and the heel-side pressure sensor 52 are also input to the inputter 43.

The battery supplies power to the walking motion assist device 1 including the drive motor 30 and the control device 40. The drive mechanism 31, which is a mechanism disposed in the shank container box 20, transmits the rotating force provided by the drive motor 30 to rotationally move the foot frame 11A relative to the shank frame 12A.

The following describes operations of the walking motion assist device 1. First, the wearer (person in gait training) inserts the wearer's foot into the foot brace 10 to be held firmly therein and fastens the shank brace 13 to the wearer's shank.

Figure 4:
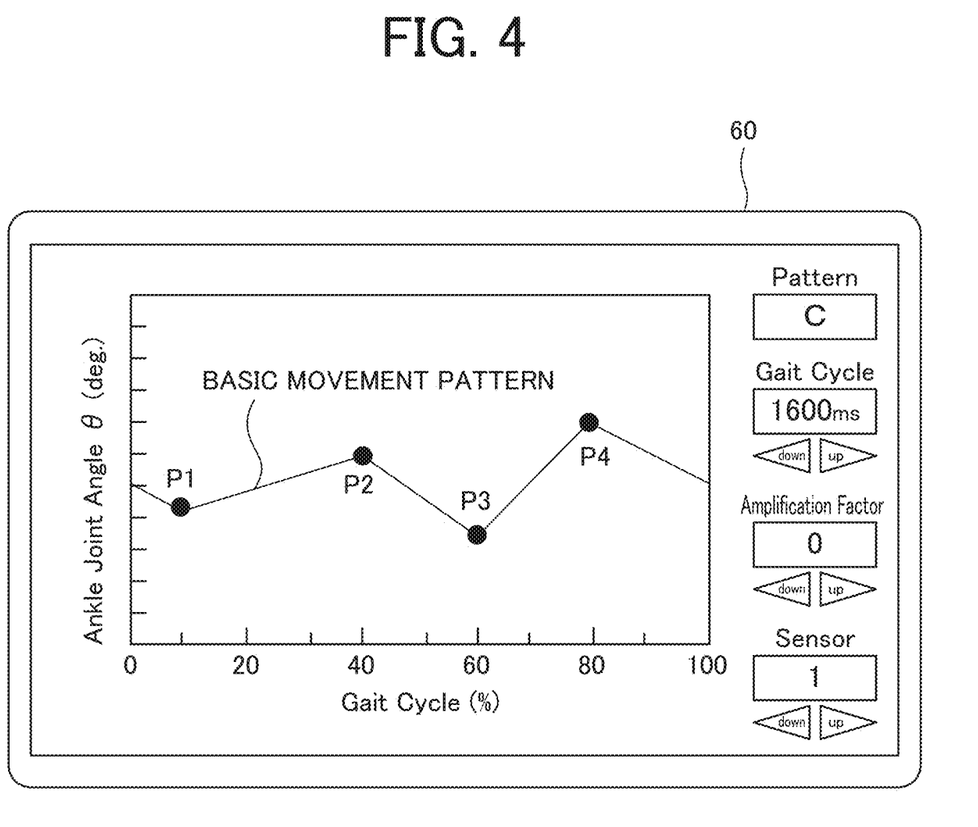
FIG. 4 illustrates a basic movement pattern shown on a display operation device.

Then, after the walking motion assist device 1 is powered on, the operator, who is a physical therapist, for example, uses the display operation device 60 to select any one suitable for the person in gait training from a plurality of basic movement patterns stored in the storage 42. The basic movement patterns each represent time-series changes in ankle joint angle in a gait cycle. For example, as illustrated in FIG. 4, the basic movement pattern is represented by a polygonal line passing through four points, P1 to P4, on the display operation device 60.

The phases at the four points P1 to P4 correspond to heel and toe contact (P1), heel off (P2), toe off (P3), and midswing (P4) in a gait cycle. The points P1, P2, P3, and P4 approximately correspond to 5 to 15%, 35 to 45%, 55 to 65%, and 75 to 85%, respectively, of the phases in a gait cycle.

It is assumed here that a gait cycle begins with heelstrike of the foot that wears the foot brace 10 and ends with heelstrike of the same foot that has taken a step. Thus, the description below assumes that a gait cycle starts at heelstrike of the foot (0% of the gait cycle in FIG. 4) and ends at heelstrike of the same foot that has taken a step (100% of the gait cycle in FIG. 4).

Since the gait cycle differs between individual persons, the walking motion assist device 1 is adjusted so that the gait cycle is suitable for the wearer. For example, the operator presses the "up" or "down" button under "Gait Cycle" illustrated in FIG. 4 to set the period of a gait cycle to a longer or shorter time, and then the control device 40 exerts control based on the newly set gait cycle.

After the wearer puts on the foot brace 10, the sensitivity of detection by the toe-side pressure sensor 51 and the heel-side pressure sensor 52 is set. Specifically, the storage 42 in the control device 40 stores the reference load, which is the load detected by either of the toe-side pressure sensor 51 and the heel-side pressure sensor 52 when the wearer is standing (in a standing position). The operator can make the reference load higher or lower by pressing the "up" or "down" button under Sensor on the display operation device 60. Then, while the wearer is in walking motion, the control device 40 recognizes that the wearer's toe or heel is on the ground when the toe-side pressure sensor 51 or the heel-side pressure sensor 52 detects a load higher than the reference load.

Note that the sensitivity of detection by the toe-side pressure sensor 51 and the heel-side pressure sensor 52 can be adjusted; the reference load can be adjusted to be higher or lower. For example, the operator can make the reference load higher or lower by pressing the "up" or "down" button under "Sensor" on the display operation device 60 illustrated in FIG. 4. Note that the present embodiment employs the control scheme in which the toe-side pressure sensor 51 is not used.

Now, the wearer in a standing position starts gait training. The person in gait training, who is in a standing position, takes a step with the person's foot that wears the foot brace 10. When the heel-side pressure sensor 52 detects that the heel of the lifted foot comes into contact with the ground, the control device 40 identifies the ankle joint angle at the time of the heel contact as the ankle joint angle at the starting point of a gait cycle, and then starts control of driving provided by the drive motor 30 based on the selected basic movement pattern.

Based on the selected basic movement pattern, the control device 40 controls angular velocities and torques provided by the drive motor 30 so that the ankle joint angles are consistent with the basic movement pattern. For example, the calculator 41 includes a built-in timer to calculate the rotational direction, the angular velocity, and the duration time for the drive motor 30 for each of the periods: 0% of gait cycle to P1, P1 to P2, P2 to P3, P3 to P4, and P4 to 100% of gait cycle, based on the selected basic movement pattern and the specified period of one cycle (1,600 ms in FIG. 4). Then, the calculator 41 controls the drive motor 30 based on the calculated information. The control device 40 also controls driving provided by the drive motor 30 so that the timing and momentum of switching from dorsiflexion to plantar flexion at P1 (heel and toe contact) are conveyed to the wearer. The control device 40 also controls driving provided by the drive motor 30 so that the timing and momentum of switching from plantar flexion to dorsiflexion at P2 (heel off) are conveyed to the wearer. The control device 40 also controls driving provided by the drive motor 30 so that the timing and momentum of switching from dorsiflexion to plantar flexion at P3 (toe off) are conveyed to the wearer. The control device 40 also controls driving provided by the drive motor 30 so that the timing and momentum of switching from plantar flexion to dorsiflexion at P4 (midswing) are conveyed to the wearer.

In sum, with reference to the basic movement pattern indicated by a polygonal line in FIG. 4, rotational driving (angular velocities and torques) provided by the drive motor 30 is controlled so that the angular velocity of the ankle joint is inverted to the positive side (dorsiflexion) at P1, inverted to the negative side (plantar flexion) at P2, inverted to the positive side (dorsiflexion) at P3, and inverted to the negative side (plantar flexion) at P4. In addition, the rotational driving (angular velocities and torques) provided by the drive motor 30 is controlled so that the angular velocity is kept unchanged in each of the periods: P1 to P2, P2 to P3, P3 to P4, and P4 to P1.

As a result, the wearer walks with a gait consistent with the time-series ankle joint angles in a gait cycle represented by the basic movement pattern. As results of detection by the rotation sensor 50, the toe-side pressure sensor 51, and the heel-side pressure sensor 52 are transmitted to the inputter 43, the control device 40 controls driving provided by the drive motor 30 at the right time depending on the state of the wearer's gait.

In addition, by controlling torques provided by the drive motor 30, the walking motion assist device 1 can allow the wearer in walking motion to forcefully disregard the time-series ankle joint angles represented by a basic movement pattern or a corrected movement pattern. The operator can set the torque provided by the drive motor 30 to a higher or lower value by pressing the "up" or "down" button under "Amplification Factor" on the display operation device 60 illustrated in FIG. 4. Based on the newly set amplification factor, the control device 40 controls the torque provided by the drive motor 30.

For example, for a human who can actively move his/her ankle joint to some extent, the training may be more efficient when the timing of switching from dorsiflexion to plantar flexion or switching from plantar flexion to dorsiflexion is merely suggested. In such cases, the training can be made more efficient without giving excessive support by setting the amplification factor to a lower value, causing the control device 40 to control the drive motor 30 so that a lower torque is produced.

In contrast, for a human who has difficulty in actively moving his/her ankle joint, enough support can be given by setting the amplification factor to a higher value, causing the control device 40 to control the drive motor 30 so that a higher torque is produced.

In this way, the walking motion assist device 1 controls torques and angular velocities applied to the ankle joint, and allows for control without using the target ankle joint angles in a gait cycle as absolute angles. In this case, ankle joint angles of the wearer in an actual walking motion may not be completely consistent with, and may deviate from, the basic movement pattern.

Figure 5:
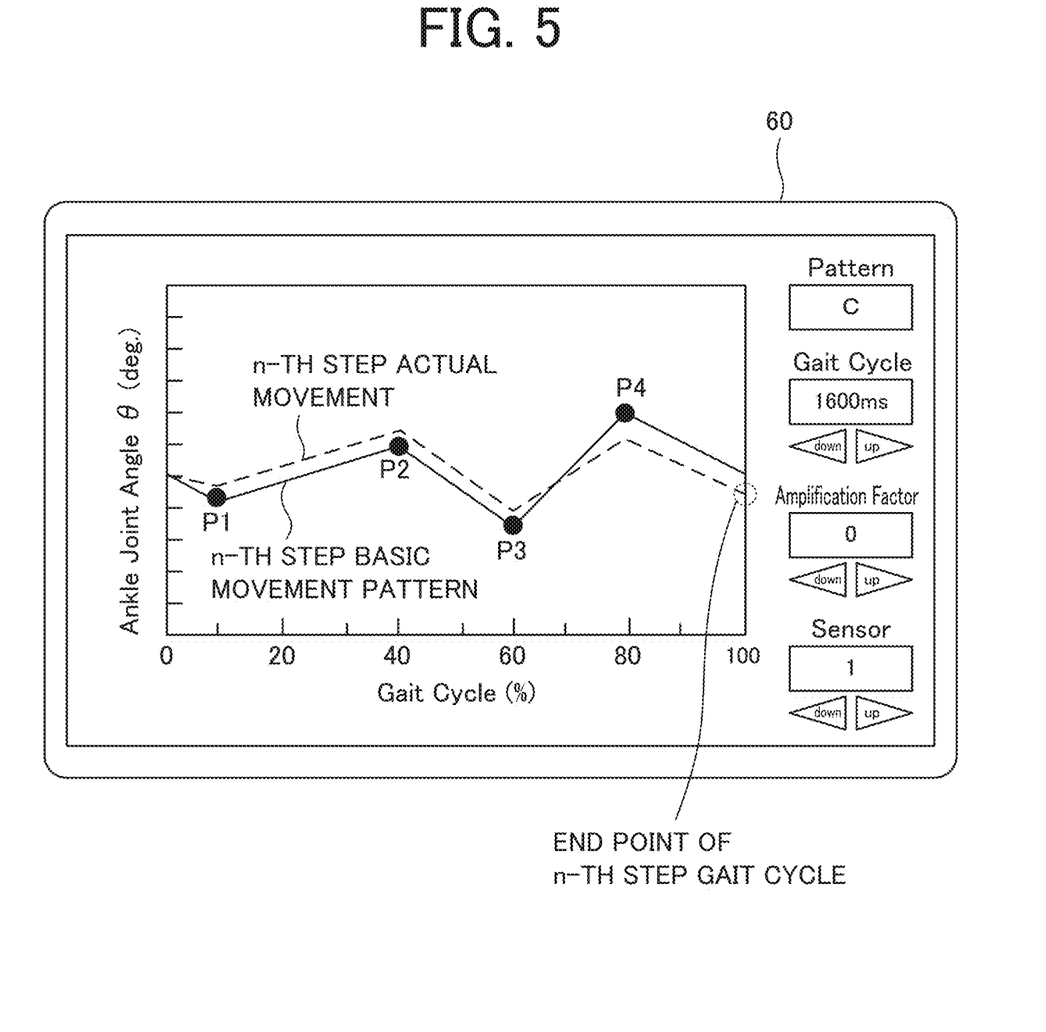
FIG. 5 illustrates a difference between a basic movement pattern for the n-th step and an actual movement during the n-th step.
Figure 6:
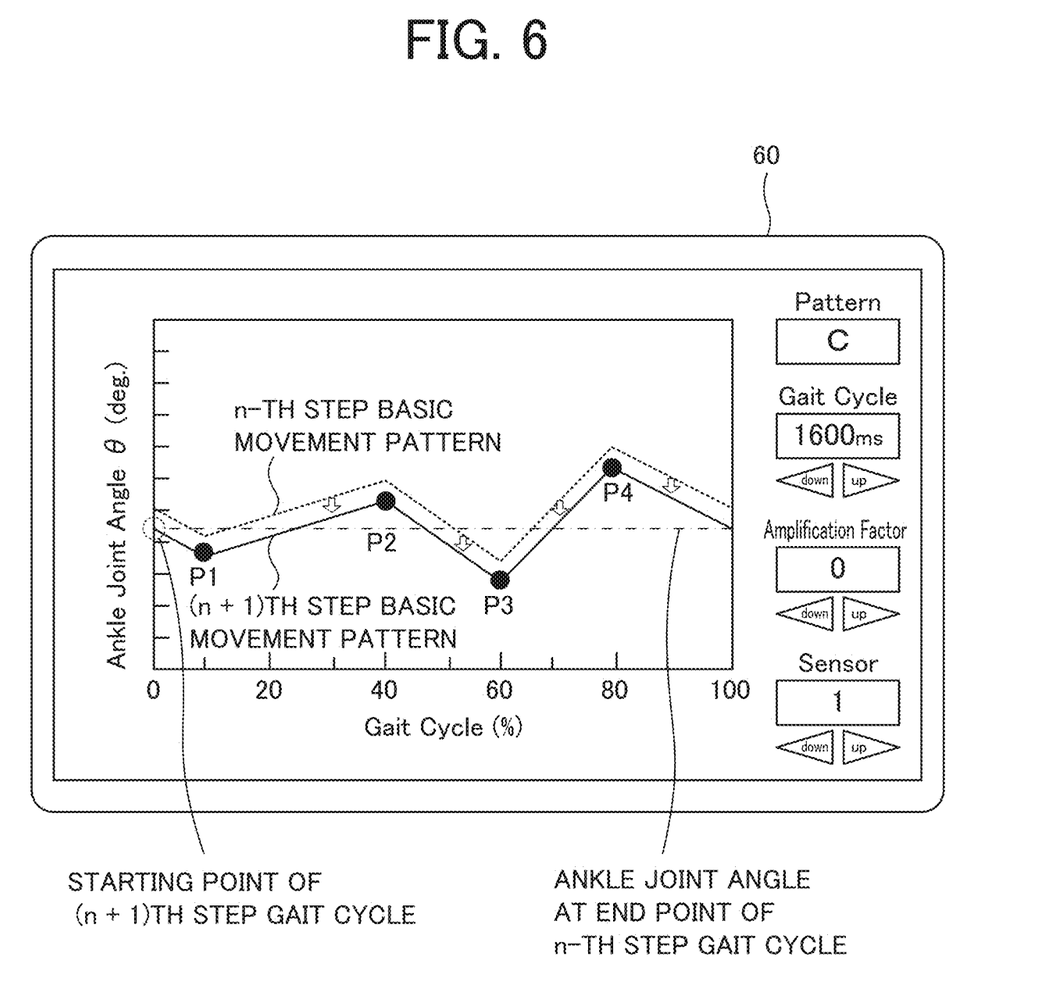
FIG. 6 illustrates an adjustment made to the basic movement pattern for the (n+1)th step.

For example, as schematically illustrated in FIG. 5, the actual movement of the walker during the n-th step may be shifted from the selected basic movement pattern, and consequently, at the end of the n-th step gait cycle, the ankle joint angle in the actual movement may be smaller than the ankle joint angle in the basic movement pattern. In this case, as illustrated in FIG. 6, the ankle joint angle in the actual movement at the end of the n-th step gait cycle is used as the ankle joint angle at the beginning of the (n+1)th step gait cycle, and thus the whole basic movement pattern is lowered. Then, based on the basic movement pattern as adjusted above, the control device 40 controls driving provided by the drive motor 30. Note that n represents a positive integer.

Likewise, when the ankle joint angle of the person in gait training in the actual movement at the end of the n-th step gait cycle is larger than the corresponding ankle joint angle in the basic movement pattern, the ankle joint angle in the actual movement at the end of the n-th step gait cycle is used as the ankle joint angle at the beginning of the (n+1)th step gait cycle, and thus the whole basic movement pattern is raised contrary to the preceding case.

In this way, the walking motion assist device 1 adjusts and controls the basic movement pattern for the (n+1)th step gait cycle by using the ankle joint angle at the end of the n-th step gait cycle as the ankle joint angle at the beginning of the (n+1)th step gait cycle. As a result, despite the fact that the gait of a walker varies between steps, the walker can do natural gait training without unwillingly following the machine.

The human gait varies with each step. Hence, when subjected to totally corrected ankle joint angles while in walking motion, the wearer feels maneuvered and finds the walking very difficult, which leads to, for example, ending up in failure, thus reducing the efficiency of rehabilitation. In contrast, the walking motion assist device 1 according to the present embodiment provides control in response to the walking motion that varies between steps, merely indicating the timing and momentum of switching from plantar flexion to dorsiflexion or from dorsiflexion to plantar flexion at each of P1 to P4, as described above. As a result, the walker feels less maneuvered by the walking motion assist device 1 and finds the walking less troublesome, which leads to higher efficiency of rehabilitation.

When the wearer, who is under control based on a basic movement pattern, is in an awkward walking motion or has some other feeling of discomfort and finds it difficult to keep walking, the operator moves vertically or horizontally the four points P1 to P4 on a polygonal line shown on the display operation device 60.

By moving each of the points P1 to P4 along a horizontal axis on the display operation device 60, the operator adjusts the timing of heel and toe contact, heel off, toe off, and midswing, that is, the timing of switching from plantar flexion to dorsiflexion or from dorsiflexion to plantar flexion corresponding to each of these points. By moving each of the points P1 to P4 along a vertical axis, the operator adjusts the angular velocity when switching from plantar flexion to dorsiflexion or from dorsiflexion to plantar flexion at each of heel and toe contact, heel off, toe off, and midswing.

Figure 7:
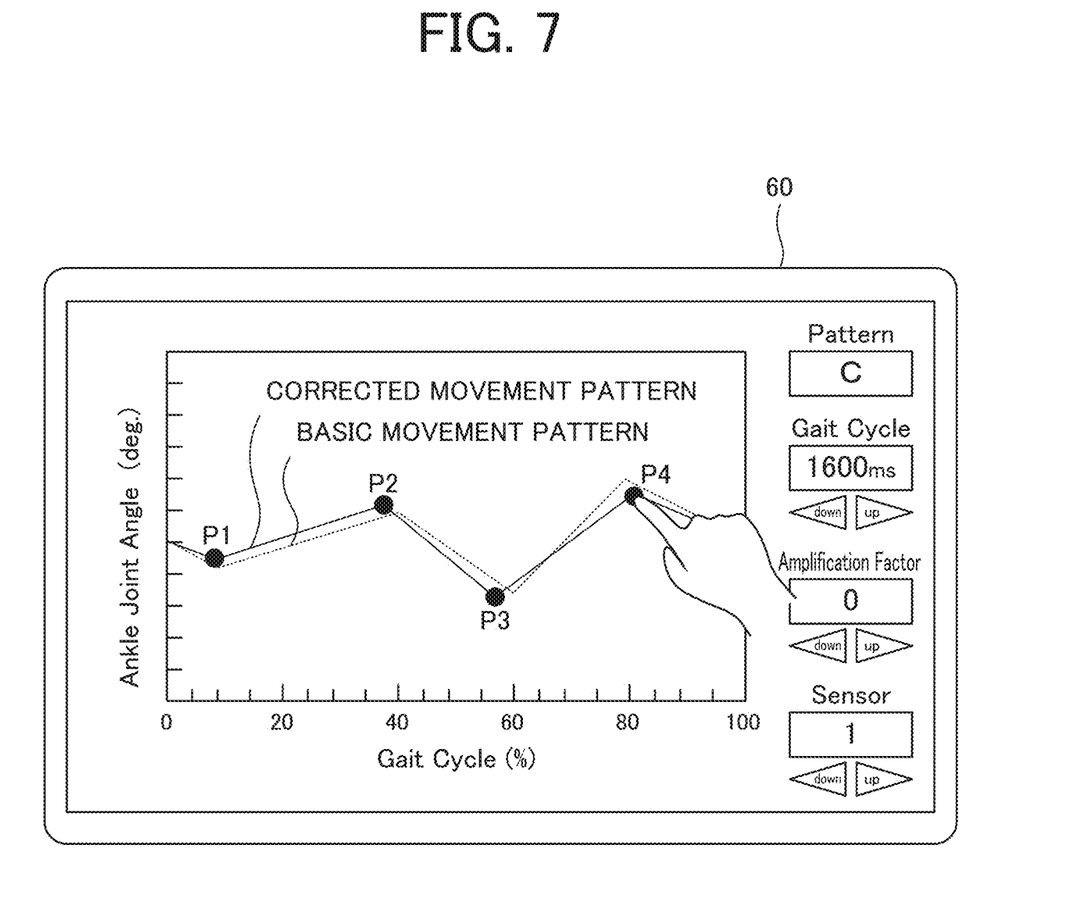
FIG. 7 illustrates correcting the basic movement pattern shown on the display operation device to create a corrected movement pattern.

The corrective information provided by the operator is sent to the inputter 43, and the calculator 41 adjusts the points P1 to P4 vertically or horizontally on the basic movement pattern to which the repositioning changes have been made. Then, the calculator 41 generates a corrected movement pattern represented by a polygonal line passing through the repositioned points P1 to P4, whereby the corrected movement pattern is displayed on the display operation device 60 as shown in FIG. 7.

By repositioning the four points on the polygonal line, the timing of switching from plantar flexion to dorsiflexion or from dorsiflexion to plantar flexion is changed for each of heel and toe contact, heel off, toe off, and midswing in the corrected movement pattern represented by a polygonal line, and, at the same time, the ankle joint angle is adjusted to have an appropriate angular velocity for each of: from heelstrike to heel and toe contact, from heel and toe contact to heel off, from heel off to toe off, from toe off to midswing, and from midswing to heelstrike.

The corrected movement pattern that has been generated is stored in the storage 42. Then, similarly to the above-described control based on a basic movement pattern, when the heel contacts the ground, the calculator 41 starts control of driving provided by the drive motor 30 based on the corrected movement pattern. Therefore, the walking motion assist device 1 achieves assisting the wearer in smooth walking.

Note that the corrected movement pattern is adjusted every gait cycle so that the actual ankle joint angle at the end of the n-th step gait cycle serves as the ankle joint angle at the beginning of the (n+1)th step gait cycle, as with the control based on a basic movement pattern described above.

Since the walking motion assist device 1 makes it possible to obtain a corrected movement pattern by moving the four points on a polygonal line representing a basic movement pattern as described above, the wearer can have a shorter waiting time for correction of the movement pattern. In addition, since both the ankle joint angle and the phase can be corrected simultaneously by an operator such as a physical therapist, the wearer can do the training efficiently.

In the example described above, control is exercised based on basic movement patterns and corrected movement patterns represented by polygonal lines. However, in other embodiments, the basic movement patterns and corrected movement patterns each may be represented by a polygonal line, a Bezier curve, or a combination thereof. In cases where a basic movement pattern is represented by a Bezier curve, the calculator 41 calculates rotational directions, angular velocities, and duration times for the drive motor 30 in a gait cycle so as to conform with the basic movement pattern, based on the selected basic movement pattern and the specified one cycle period. Then, the calculator 41 controls the drive motor 30 based on the calculated information. Although the display operation device 60 described in the example above shows a single gait cycle, the display operation device 60 may be configured to show a plurality of gait cycles.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2016-111378, filed on Jun. 2, 2016, the entire disclosure of which is incorporated by reference herein.

REFERENCE SIGNS LIST

1 Walking motion assist device
10 Foot brace
11A, 11B Foot frame
12A, 12B Shank frame
13 Shank brace
20 Shank container box
30 Drive motor
31 Drive mechanism
40 Control device
41 Calculator
42 Storage
43 Inputter
50 Rotation sensor
51 Toe-side pressure sensor
52 Heel-side pressure sensor
60 Display operation device
70 Waist brace
71 Waist container box
P1 Heel and toe contact
P2 Heel off
P3 Toe off
P4 Midswing

The invention claimed is:

1. A walking motion assist device for assisting a wearer in rotationally moving an ankle joint of the wearer, the walking motion assist device comprising:
a drive motor;
a drive shaft that is capable of rotating coaxially with the ankle joint by way of the drive motor;
a control device that controls driving provided by the drive motor;
a storage that stores a basic movement pattern and a corrected movement pattern that represent time-series changes in ankle joint angle in a gait cycle; and
a calculator that obtains the corrected movement pattern by correcting the basic movement pattern based on input by an operator,
wherein the basic movement pattern is displayed on a display operation device by a polygonal line, a Bézier curve, or a combination of the polygonal line and the Bézier curve, each of the polygonal line, the Bézier curve, and the combination of the polygonal line and the Bézier curve includes only four points serving as inflection points corresponding to heel and toe contact, heel off, toe off, and midswing in the gait cycle in an order, of the heel and toe contact, the heel off, the toe off, and the midswing,
wherein the calculator generates the corrected movement pattern corrected by adjusting positions of the inflection points on the basic movement pattern, and
wherein the control device controls driving provided by the drive motor based on the corrected movement pattern.

2. The walking motion assist device according to claim 1 wherein the control device controls an angular velocity of the ankle joint in conformance with the basic movement pattern or the corrected movement pattern.

3. The walking motion assist device according to claim 1, further comprising:
a heel-side pressure sensor that detects heelstrike and heel off of the wearer; and a toe-side pressure sensor that detects toe contact and toe off of the wearer,
wherein the heel-side pressure sensor and the toe-side pressure sensor detect a load of the heel and a load of the toe, respectively, when the wearer is in a standing position, and
wherein, based on the load detected when the wearer is in the standing position, a state of the heelstrike, the toe contact, the heel off, and the toe off of the wearer in walking motion is detected.

4. The walking motion assist device according to claim 3, wherein, as a starting point of a gait cycle, from a point of time when the heel-side pressure sensor detects the heelstrike of the wearer, the control device controls driving provided by the drive motor based on the basic movement pattern or the corrected movement pattern.

5. The walking motion assist device according to claim 3, further comprising:
a rotation sensor that detects an ankle joint angle of the wearer,
wherein, assuming that a starting point and an end point of a single step gait cycle correspond to the heelstrike and the next heelstrike, respectively, the control device uses the ankle joint angle detected by the rotation sensor at the end point of an n-th step as the ankle joint angle at the starting point of an (n+1)th step to adjust the basic movement pattern or the corrected movement pattern for the (n+1)th step and controls the drive motor, where n represents a positive integer.

* * * * *